(12) United States Patent
Hashimoto et al.

(10) Patent No.: US 8,759,042 B2
(45) Date of Patent: Jun. 24, 2014

(54) METHOD FOR PRODUCTION OF AMINO ACID

(75) Inventors: Shin-ichi Hashimoto, Hofu-shi (JP); Koji Harada, Tokyo (JP); Nozomu Kamada, Takatsuki (JP); Tetsuya Nishitani, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 1169 days.

(21) Appl. No.: 12/374,991

(22) PCT Filed: Jul. 25, 2007

(86) PCT No.: PCT/JP2007/064547
§ 371 (c)(1),
(2), (4) Date: Jan. 23, 2009

(87) PCT Pub. No.: WO2008/013187
PCT Pub. Date: Jan. 31, 2008

(65) Prior Publication Data
US 2009/0258399 A1   Oct. 15, 2009

(30) Foreign Application Priority Data
Jul. 25, 2006 (JP) ................. 2006-201950

(51) Int. Cl.
C12P 13/04 (2006.01)
C12N 9/00 (2006.01)
C12N 1/20 (2006.01)
C12N 15/00 (2006.01)
C07H 21/02 (2006.01)

(52) U.S. Cl.
USPC ... 435/106; 435/183; 435/252.33; 435/252.8; 435/320.1; 536/23.1

(58) Field of Classification Search
None
See application file for complete search history.

(56) References Cited

FOREIGN PATENT DOCUMENTS

| JP | 2005-224163 A | 7/2005 |
|---|---|---|
| WO | WO 95/04074 A1 | 2/1995 |
| WO | WO 99/02721 A1 | 1/1999 |
| WO | WO 03/46184 A1 | 6/2003 |
| WO | WO 2004/056996 A2 | 7/2004 |
| WO | WO 2007/119574 A2 | 10/2007 |

OTHER PUBLICATIONS

GenEmbl accession # AF031251 Jan. 6, 2005.*
Liu et al., *The Journal of Biological Chemistry*, 272(28): 17502-17510 (1997).
Romeo et al., *Journal of Bacteriology*, 175(15): 4744-4755 (Aug. 1993).
Tatarko et al., *Current Microbiology*, 43: 26-32 (2001).
Weilbacher et al., *Molecular Microbiology*, 48(3): 657-670 (2003).
Kanehisa Laboratories, "Arginine and Proline Metabolism," downloaded from http://www.genome.jp/kegg-bin/show_pathway?eco00330+b3957 (May 29, 2012).

* cited by examiner

*Primary Examiner* — Oluwatosin Ogunbiyi
(74) *Attorney, Agent, or Firm* — Leydig, Voit & Mayer, Ltd.

(57) ABSTRACT

The invention provides a microorganism belonging to Enterobacteriaceae in which a function of CsrC RNA has been decreased or lost, and which has the ability to produce and accumulate an amino acid, and a process in which the microorganism is cultured in a medium to produce and accumulate the amino acid in the culture, and the amino acid is recovered from the culture.

5 Claims, No Drawings

METHOD FOR PRODUCTION OF AMINO ACID

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,729 bytes ASCII (Text) file named "704376SequenceListing.txt," created Jan. 23, 2009.

TECHNICAL FIELD

The present invention relates to a method of producing an L-amino acid.

BACKGROUND ART

In the fermentative production of an amino acid generally using a microorganism belonging to the genus *Escherichia* or a microorganism such as a coryneform bacterium, as typified by the genus *Corynebacterium*, glucose serves as the main raw material to supply carbon for both the growth of the microorganism and the production of the amino acid.

While glucose is metabolized to various compounds mainly via the glycolytic system and the pentose phosphate pathway, the metabolism involving carbon is known to include gluconeogenesis that reverses the glycolytic system; when a microorganism grows using a carbon source like acetic acid, for example, the necessary metabolites for the growth must be biosynthesized via the gluconeogenetic pathway. Hence, the metabolism from glucose is expressed as the sum of both the metabolic pathways of glycolysis and gluconeogenesis.

Gluconeogenesis is necessary for microorganisms to survive in various environments, and it is known that the balance between the glycolytic system and gluconeogenesis is regulated according to environmental factors. It has been reported that in microorganisms belonging to *Escherichia coli*, the glycolysis/gluconeogenesis balance is regulated mainly by the Csr (Carbon Storage Regulator) system (non-patent document 1). It is a regulatory protein known as CsrA protein that plays the central role in the Csr system, having the function of binding to the 5'-noncoding region of target messenger RNA to increase the translation of glycolytic system enzymes and reduce the translation of gluconeogenesis enzymes. Recently, deficiency of the csrA gene was reported to improve L-phenylalanine productivity, and this is attributed to enhancement of the shikimic pathway, which is essential for L-phenylalanine production, as a result of an increased supply of phosphoenolpyruvic acid due to decreased glycolysis and increased gluconeogenesis (non-patent document 2).

Meanwhile, it is known that the Csr system includes, as regulatory factors, CsrB RNA (non-patent document 3) and CsrC RNA (non-patent document 1) which bind to CsrA protein to reduce its function. CsrB RNA and CsrC RNA are both noncoding small RNAs, and are known to have, as CsrA protein binding sites, 18 and 9 conserved nucleotide sequences comprising the nucleotide sequences shown by SEQ ID NO:1, 2 and 3, respectively.

However, to date, it has not been reported that amino acid productivity was improved by modifying, particularly deleting, a function of a small RNA involved in the regulation of the glycolytic system/gluconeogenesis balance, such as CsrB RNA or CsrC RNA.

Non-patent document 1: Journal of Bacteriology, 1993, vol. 175, p. 4744-4755
Non-patent document 2: Current Microbiology, 2001, vol. 43, p. 26-32
Non-patent document 3: The Journal of Biological Chemistry, 1997, vol. 272, p. 17502-17510

DISCLOSURE OF THE INVENTION

Problems to be Solved by the Invention

It is an object of the present invention to provide an industrially advantageous method of producing an L-amino acid.

Means of Solving the Problems

The present invention relates to (1) to (10) below.
(1) A microorganism belonging to Enterobacteriaceae in which a function of CsrB RNA or CsrC RNA has been reduced or lost, and which has the ability to produce and accumulate an amino acid.
(2) The microorganism of (1) above, wherein the microorganism in which a function of CsrB RNA or CsrC RNA has been reduced or lost is a microorganism lacking a part or all of the region csrB gene or the csrC gene.
(3) The microorganism of (1) or (2) above, wherein the CsrB RNA and CsrC RNA are transcripts of DNAs consisting of the nucleotide sequences shown by SEQ ID NO:78 and 79, respectively.
(4) The microorganism of any one of (1) to (3) above, wherein the microorganism belonging to Enterobacteriaceae is a microorganism belonging to any one of the genus *Escherichia*, the genus *Salmonella*, the genus *Enterobacter*, the genus *Serratia*, the genus *Yersinia* and the genus *Erwinia*.
(5) The microorganism of (4) above, wherein the microorganism belonging to the genus *Escherichia* is *Escherichia coli*.
(6) The microorganism described in any one of (1) to (5) above, wherein the amino acid is an amino acid selected from the group consisting of L-alanine, L-serine, L-cysteine, L-glutamic acid, L-glutamine, L-proline, L-ornithine, L-citrulline, L-arginine, L-aspartic acid, L-asparagine, L-homoserine, L-threonine, L-methionine, L-lysine, L-isoleucine, L-valine, L-leucine, L-tryptophan, L-tyrosine, L-phenylalanine and L-histidine.
(7) The microorganism described in any one of (1) to (5) above, wherein the amino acid is an amino acid selected from the group consisting of L-alanine, L-glutamic acid, L-glutamine, L-proline, L-ornithine, L-citrulline, L-arginine, L-isoleucine, L-valine and L-leucine.
(8) A process for producing an amino acid, which comprises culturing the microorganism described in any one of (1) to (5) above in a medium to produce and accumulate the amino acid in the medium, and recovering the amino acid from the medium.
(9) The process of (8) above, wherein the amino acid is an amino acid selected from the group consisting of L-alanine, L-serine, L-cysteine, L-glutamic acid, L-glutamine, L-proline, L-ornithine, L-citrulline, L-arginine, L-aspartic acid, L-asparagine, L-homoserine, L-threonine, L-methionine, L-lysine, L-isoleucine, L-valine, L-leucine, L-tryptophan, L-tyrosine, L-phenylalanine and L-histidine.
(10) The process of (8) above, wherein the amino acid is an amino acid selected from the group consisting of L-alanine, L-glutamic acid, L-glutamine, L-proline, L-ornithine, L-citrulline, L-arginine, L-isoleucine, L-valine and L-leucine.

Effect of the Invention

According to the present invention, an L-amino acid can be produced industrially advantageously.

BEST MODE FOR CARRYING OUT THE INVENTION

1. Microorganisms of the Present Invention
(1) CsrB RNA or CsrC RNA

In the present invention, CsrB RNA or CsrC RNA refers to an RNA which is a transcript of a DNA consisting of the nucleotide sequence shown by SEQ ID NO:78 or 79, or a homologue of a transcript of a DNA consisting of the nucleotide sequence shown by SEQ ID NO:78 or 79, which consists of a nucleotide sequence having an identity of 80% or more, preferably 85% or more, more preferably 90% or more, still more preferably 95% or more, particularly preferably 97% or more, and most preferably 98% or more, to the DNA, and which has the function of binding to CsrA protein or a homologue thereof to suppress the activity thereof.

As CsrA protein, an *Escherichia coli*-derived protein consisting of the amino acid sequence shown by GENBANK Accession no. AAC75738, *Salmonella typhimulium*-derived CsrA proteins consisting of the amino acid sequences shown by GENBANK Accession no. AAG35184 and AAF80413, an *Erwinia carotovora*-derived CsrA protein consisting of the amino acid sequence shown by GENBANK Accession no. CAG76264, and a *Yersinia pseudotuberculosis*-derived CsrA protein consisting of the amino acid sequence shown by GENBANK Accession no. CAH20066 can be mentioned; as a homologue of CsrA protein, a protein consisting of an amino acid sequence having an identity of 80% or more, preferably 85% or more, more preferably 90% or more, still more preferably 95% or more, particularly preferably 97% or more, and most preferably 98% or more, to the amino acid sequence shown by GENBANK Accession no. AAC75738, and having substantially the same activity as that of an *Escherichia coli*-derived CsrA protein, can be mentioned.

As examples of CsrB RNA, an *Escherichia coli*-derived RNA being a transcript of a DNA consisting of the nucleotide sequence shown by SEQ ID NO:78, an *Salmonella typhimulium*-derived RNA being a transcript of a DNA consisting of the nucleotide sequence shown by GENBANK Gene ID 1254489, an *Erwinia carotovora*-derived RNA being a transcript of a DNA consisting of the nucleotide sequence shown by GENBANK Gene ID 2884449, and a *Yersinia pseudotuberculosis*-derived RNA being a transcript of a DNA consisting of the nucleotide sequence shown by GENBANK Gene ID 2955376 can be mentioned.

As examples of CsrC RNA, an *Escherichia coli*-derived RNA being a transcript of a DNA consisting of the nucleotide sequence shown by SEQ ID NO:79, and a *Yersinia pseudotuberculosis*-derived RNA being a transcript of a DNA consisting of the nucleotide sequence shown by GENBANK Gene ID 2955134 can be mentioned.

(2) Microorganisms belonging to Enterobacteriaceae wherein a function of CsrB RNA or CsrC RNA has been reduced or lost As a microorganism belonging to Enterobacteriaceae wherein a function of CsrB RNA or CsrC RNA has been reduced or lost, a microorganism wherein CsrB RNA or CsrC RNA is not transcribed from the csrB gene or the csrC gene because of the presence of a nucleotide deletion, substitution or addition in the nucleotide sequence of the csrB gene or the csrC gene on chromosomal DNA, or a microorganism wherein the function of suppressing the activity of CsrA protein, possessed by a transcript of the gene, has been reduced or lost, can be mentioned.

As the csrB gene or the csrC gene, a DNA consisting of a transcription region corresponding to CsrB RNA or CsrC RNA and a transcription regulatory region such as a promoter of the gene, preferably a DNA consisting of a transcription region corresponding to CsrB RNA or CsrC RNA, can be mentioned.

As a microorganism wherein the function of CsrB RNA or CsrC RNA to suppress the activity of CsrA protein has been reduced or lost, a microorganism wherein the activity of CsrA protein in the cells thereof has been elevated 1.5 times or more, preferably 2 times or more, and more preferably 4 times or more, compared with the activity of CsrA protein in microbial cells having the normal type of CsrB RNA or CsrC RNA without a nucleotide deletion, substitution or addition because of a reduction or loss of the binding activity of the RNA to CsrA protein, can be mentioned.

The above-described microorganism belonging to Enterobacteriaceae may be any Enterobacteriaceae wherein a function of CsrB RNA or CsrC RNA has been reduced or lost; for example, a microorganism belonging to the genus *Escherichia*, the genus *Salmonella*, the genus *Enterobacter*, the genus *Serratia*, the genus *Erwinia* or the genus *Yersinia*, preferably a microorganism belonging to the genus *Escherichia*, and more preferably a microorganism belonging to *Escherichia coli*, can be mentioned.

(3) Process for Producing a Microorganism of the Present Invention

While a microorganism of the present invention can be prepared by a method wherein a function of CsrB RNA or CsrC RNA of a microorganism belonging to Enterobacteriaceae is reduced or lost, the same can also be prepared by 1) a method using as the microorganism a microorganism essentially having the ability to produce and accumulate an amino acid, or a microorganism given the ability to produce and accumulate an amino acid, or 2) a method wherein the ability to produce and accumulate an amino acid is introduced into a microorganism wherein a function of CsrB RNA or CsrC RNA has been reduced or lost.

A microorganism wherein a function of CsrB RNA or CsrC RNA has been reduced or lost can be prepared by a method wherein the csrB gene or the csrC gene of a mutated form with its function reduced or lost, possessed by an existing microorganism, is accumulated in a single microorganism by transduction using a phage [J. H. Miller, Experiments in Molecular Genetics, Cold Spring Harbor Lab. (1972)], a method wherein a microorganism is treated by UV irradiation, a mutagenic agent and the like, after which a strain wherein a function of CsrB RNA or CsrC RNA has been reduced or lost is selected, a method wherein a nucleotide deletion, substitution or addition is introduced into the nucleotide sequence of the csrB gene or the csrC gene on the chromosomal DNA of the microorganism, or the like.

The region into which a nucleotide deletion, substitution or addition is introduced is not subject to limitations, as long as the region is in the csrB gene or the csrC gene; a transcription region of CsrB RNA or CsrC RNA and a transcription regulatory region such as a promoter of the gene can be mentioned, a transcription region of CsrB RNA or CsrC RNA being preferable.

As a transcription regulatory region, a DNA consisting of 50 nucleotides upstream of the 5' end of a transcription region on chromosomal DNA can be mentioned, a region corresponding to the −10 and −35 regions being preferable.

Introduction of a nucleotide deletion, substitution or addition into a transcription region is not subject to limitations with respect to the kind(s) and number of nucleotides, provided that the nucleotide deletion, substitution or addition reduces or loses a function of the transcript; as a nucleotide deletion, deletion of preferably 10 nucleotides or more, more preferably 20 nucleotides or more, still more preferably 100 nucleotides or more, and particularly preferably 200 nucleotides or more, of a part of a transcription region, and most preferably of all of a transcription region, can be mentioned. As a nucleotide substitution, substitution of a nucleotide within the 150th from the 5' end of a transcription region, preferably a nucleotide within the 100th, more preferably a nucleotide within the 50th, particularly preferably a nucleotide within the 30th, and most preferably a nucleotide within the 20th, to introduce a nonsense codon can be mentioned. As a nucleotide addition, addition of 50 nucleotides or more, preferably 100 nucleotides or more, more preferably 200 nucleotides or more, still more preferably 500 nucleotides or more, and particularly preferably 1 kb or more, of a DNA fragment just after a nucleotide within the 150th nucleotide from the 5' end of a transcription region, preferably a nucleotide within the 100th, more preferably a nucleotide within the 50th, particularly preferably a nucleotide within the 30th, and most preferably a nucleotide within the 20th, can be mentioned; insertion of a drug resistance gene such as the chloramphenicol resistance gene or the kanamycin resistance gene being particularly preferable.

As a method of introducing a nucleotide deletion, substitution or addition into a gene of the chromosomal DNA of a microorganism, a method based on homologous recombination can be mentioned. As a method based on general homologous recombination, a method using a plasmid for homologous recombination that can be prepared by ligating a mutated gene including a nucleotide deletion, substitution or addition into a plasmid DNA having a drug resistance gene, which plasmid is incapable of self-replication in the host cell into which a nucleotide deletion or the like is to be introduced, can be mentioned; as a method based on homologous recombination in common use for *Escherichia coli*, a method wherein a nucleotide deletion, substitution or addition is introduced by means of a lambda phage homologous recombination system [Proc. Natl. Acad. Sci. USA, 97, 6641-6645 (2000)] can be mentioned.

As a method based on homologous recombination, a method can be mentioned, the method wherein i) the plasmid for homologous recombination is introduced into a host cell by a conventional method, after which a transformed strain having the plasmid for homologous recombination integrated into the chromosomal DNA by homologous recombination is selected with drug resistance as an index, ii) the transformed strain obtained is cultured in a medium that does not contain the drug for several hours to 1 day, after which the culture is applied on an agar medium containing the drug and an agar medium not containing the drug, and iii) a strain that does not grow on the former medium, but can grow on the latter medium, is selected, whereby a strain undergoing second homologous recombination on the chromosomal DNA is obtained. By determining the nucleotide sequence of the region in which the gene including a deletion or the like on the chromosomal DNA is present, it can be confirmed that a nucleotide deletion, substitution or addition has been introduced into the desired gene on the chromosomal DNA.

A method of introducing a nucleotide deletion, substitution or addition by means of a lambda phage homologous recombination system can be used for a microorganism belonging to the genus *Escherichia* having the ability to uptake linear DNA, preferably *Escherichia coli*, more preferably *Escherichia coli* that expresses λ phage-derived recombination proteins (Red recombination system).

As *Escherichia coli* that expresses the λRed recombination system, an *Escherichia coli* JM101 strain containing pKD46 [available from the *Escherichia coli* Genetic Stock Center (Yale University, USA)], a plasmid DNA having the λRed recombination system gene, and the like can be mentioned.

In the methods described in 1) and 2) above, the ability to produce and accumulate an amino acid can be conferred by any method; many reports have been made to date concerning methods for producing a microorganism that produces a desired amino acid, and any publicly known method can be used to produce a microorganism of the present invention.

Examples of such publicly known methods include (a) a method wherein at least one mechanism for regulating amino acid biosynthesis is weakened or eliminated, (b) a method wherein the expression of at least one enzyme involved in amino acid biosynthesis is enhanced, (c) a method wherein the copy number of at least one enzyme gene involved in amino acid biosynthesis is increased, (d) a method wherein at least one metabolic pathway that branches from the biosynthesis pathway of an amino acid to a metabolite other than the amino acid is weakened or blocked, and (e) a method wherein a cell strain which is highly resistant to amino acid analogues than the wild-type strain is selected, and the like; these publicly known methods can be used singly or in combination.

The above (a) is described in, for example, Agric. Biol. Chem., 43, 105-111 (1979), J. Bacteriol., 110, 761-763 (1972) and Appl. Microbiol. Biotechnol., 39, 318-323 (1993) and elsewhere; the above (b) is described in, for example, Agric. Biol. Chem., 43, 105-111 (1979) and J. Bacteriol., 110, 761-763 (1972) and elsewhere; the above (c) is described in, for example, Appl. Microbiol. Biotechnol., 39, 318-323 (1993) and Agric. Biol. Chem., 39, 371-377 (1987) and elsewhere; the above (d) is described in, for example, Appl. Environ. Micribiol., 38, 181-190 (1979) and Agric. Biol. Chem., 42, 1773-1778 (1978) and elsewhere; the above (e) is described in, for example, Agric. Biol. Chem., 36, 1675-1684 (1972), Agric. Biol. Chem., 41, 109-116 (1977), Agric. Biol. Chem., 37, 2013-2023 (1973) and Agric. Biol. Chem., 51, 2089-2094 (1987) and elsewhere. By reference to these documents and the like, microorganisms having the ability to produce and accumulate various amino acids can be prepared.

Regarding methods of preparing a microorganism having the ability to produce an amino acid based on any one of the above (a) to (e), or a combination thereof, many examples are given in Biotechnology 2nd ed., Vol. 6, Products of Primary Metabolism (VCH Verlagsgesellschaft mbH, Weinheim, 1996) sections 14a and 14b, Advances in Biochemical Engineering/Biotechnology 79, 1-35 (2003), and Aminosan Hakkou, Japan Scientific Societies Press, Hiroshi Aida et al. (1986); in addition, many reports are available on methods of preparing a microorganism having the ability to produce an amino acid, including JP-A-2003-164297, Agric. Biol. Chem., 39, 153-160 (1975), Agric. Biol. Chem., 39, 1149-1153 (1975), JP-A-58-13599, J. Gen. Appl. Microbiol., 4, 272-283 (1958), JP-A-63-94985, Agric. Biol. Chem., 37, 2013-2023 (1973), WO97/15673, JP-A-56-18596, JP-A-56-144092 and JP-A-2003-511086; by reference to the above documents and the like, a microorganism having the ability to produce and accumulate various amino acids can be prepared.

Specific examples of microorganisms having the ability to produce and accumulate an amino acid include L-glutamic acid producing strains such as FERM BP-5807 and ATCC13032, L-glutamine producing strains such as FERM P-4806 and ATCC14751, L-threonine producing strains such as ATCC21148, ATCC21277 and ATCC21650, L-lysine producing strains such as FERM P-5084 and ATCC13286, L-methionine producing strains such as FERM P-5479, VKPM B-2175 and ATCC21608, L-isoleucine producing strains such as FERM BP-3757 and ATCC14310, L-valine producing strains such as ATCC13005 and ATCC19561, L-leucine producing strains such as FERM BP-4704 and ATCC21302, L-alanine producing strains such as FERM BP-4121 and ATCC15108, L-serine producing strains such as ATCC21523 and FERM BP-6576, L-proline producing strains such as FERM BP-2807 and ATCC19224, L-arginine producing strains such as FERM P-5616 and ATCC21831, L-ornithine producing strains such as ATCC13232, L-histidine producing strains such as FERM BP-6674 and ATCC21607, L-tryptophan producing strains such as DSM10118, DSM10121, DSM10123 and FERM BP-1777, L-phenylalanine producing strains such as ATCC13281 and ATCC21669, L-tyrosine producing strains such as ATCC21652, L-cysteine producing strains such as W3110/pHC34 (described in JP-A-2003-511086), L-4-hydroxyproline producing strains such as *Escherichia coli* SOLR/pRH71 described in WO96/27669, L-3-hydroxyproline producing strains such as FERM BP-5026 and FERM BP-5409, and L-citrulline producing strains such as FERM P-5643 and FERM P-1645.

The aforementioned strains represented by FERM number can be obtained from the International Patent Organism Depositary, National Institute of Advanced Industrial Science and Technology (Japan), the strains represented by ATCC number from the American Type Culture Collection (USA), the strains represented by VKPM number from the Russian National Collection of Industrial Microorganisms (Russia), and the strains represented by DSM number from Deutsche Sammlung von Mikroorganismen und Zellkulturen (Germany).

The fact that a microorganism wherein a function of CsrB RNA or CsrC RNA has been reduced or lost, obtained by a method described above, has an increased ability to produce and accumulate an amino acid, compared with the parent strain showing normal functioning of CsrB RNA or CsrC RNA, can be easily confirmed by culturing the microorganism in a medium to produce and accumulate the amino acid in the medium, and analyzing the amino acid by a publicly known method, for example, HPLC-based analysis or bioassay or the like.

As a microorganism wherein a function of CsrB RNA or CsrC RNA has been decreased or lost, which produces an amino acid, which can be prepared by a method described above, *Escherichia coli* RE7ΔcsrB, *Escherichia coli* RE7ΔcsrC and the like can be mentioned.

2. Process for Production of the Present Invention

By culturing a microorganism of the present invention described in 1 above in a medium to produce and accumulate an amino acid in the medium, and recovering the amino acid from the medium, the amino acid can be produced.

As the amino acid, an amino acid selected from the group consisting of L-alanine, L-serine, L-cysteine, L-glutamic acid, L-glutamine, L-proline, L-ornithine, L-citrulline, L-arginine, L-aspartic acid, L-asparagine, L-homoserine, L-threonine, L-methionine, L-lysine, L-isoleucine, L-valine, L-leucine, L-tryptophan, L-tyrosine, L-phenylalanine and L-histidine can be mentioned. A particularly preferable amino acid is an amino acid selected from the group consisting of L-alanine, L-glutamic acid, L-glutamine, L-proline, L-ornithine, L-citrulline, L-arginine, L-isoleucine, L-valine and L-leucine, which are biosynthesized via pyruvic acid as an intermediate.

The medium used in the process for production of the present invention may be any of a synthetic medium and a natural medium, as far as it contains nutrients that are necessary for the growth of the microorganism of the present invention, and for amino acid biosynthesis, such as a carbon source, a nitrogen source, an inorganic salt, and a vitamin.

As the carbon source, which may be any carbon source that can be utilized by the microorganism used, saccharides such as glucose and fructose, alcohols such as ethanol and glycerol, organic acids such as acetic acid and the like can be mentioned.

As the nitrogen source, ammonia, ammonium salts such as ammonium sulfate, nitrogen compounds such as amines, natural nitrogen sources such as peptone and soybean hydrolyzates, and the like can be mentioned.

As the inorganic salt, potassium phosphate, magnesium sulfate, sodium chloride, ferrous sulfate, potassium carbonate and the like can be mentioned.

As the vitamin, biotin, thiamin and the like can be mentioned. Furthermore, as required, substances required by the microorganisms of the present invention to grow (for example, an amino acid required in the case of a microorganism with amino acid auxotrophy) may be added.

The culturing is preferably performed under aerobic conditions like shaking culture or aerating and agitating culture. Culturing temperature is 20 to 50° C., preferably 20 to 42° C., and more preferably 28 to 38° C. The pH during the culturing is 5 to 9, preferably 6 to 7.5. Culturing time is 5 hours to 5 days, preferably 16 hours to 3 days.

An amino acid accumulated in the culture can be recovered by an ordinary method of purification. For example, L-arginine can be recovered, after completion of the culturing, by removing cells and solid matter from the culture by centrifugation and the like, and then performing ion exchange, concentration, and crystal fractionation.

The present invention is hereinafter described in more detail by means of the following Examples, which, however, never limit the scope of the invention.

EXAMPLE 1

Preparation of Microorganism Having the Ability to Produce L-Arginine

By allowing the csrB gene and the csrC gene to be deleted from an *Escherichia coli* having the ability to produce and accumulate L-arginine wherein the argR gene, which is a repressor gene for the L-arginine biosynthesis gene on the chromosomal DNA of the *Escherichia coli* W3110 strain, the argK gene, which is involved in L-arginine uptake, and the astA gene, the speAB gene and the oat gene (also called ygjG gene) which are involved in L-arginine degradation, are deleted, and wherein a desensitization mutation has been introduced into the argA gene, which is the L-arginine biosynthesis gene, a microorganism of the present invention was prepared.

Since N-acetylglutamic acid synthase, encoded by the argA gene, is known to undergo feedback inhibition by L-arginine, Y19C mutation, which has been reported to be a desensitization mutation that confers resistance to the feedback inhibition into the argA gene (see Rajagopal, B. S., De Ponte, J. 3rd., Tuchman, M., Malamy, M. H., Applied and Environmental Microbiology, Vol. 64. 1805-1811, 1998) was introduced into the argA gene.

(1) Preparation of Streptomycin-resistant Strain

Gene deletion and gene substitution for *Escherichia coli* were achieved by homologous recombination using the λred System [Datsenko, K. A., Warner, B. L., Proceedings of the National Academy of Science of the United States of America, Vol. 97. 6640-6645 (2000)]. The plasmid pKD46 described below was used after being extracted by a publicly known method from an *Escherichia coli* strain containing the plasmid obtained from the *Escherichia coli* Genetic Stock Center (Yale University, USA).

By introducing the K43T mutation in the rpsL gene, reported as a streptomycin resistance mutation in *Escherichia coli* [Hosaka, T., Tamehiro, N., Chumpolkulwong, N., Hori-Takemoto, C. Shirouzu, M., Yokoyama, S., Ochi, K., Molecular Genetics and Genomics, Vol. 271. 317-324 (2004)], into the *Escherichia coli* W3110 strain by the method described below, a streptomycin-resistant strain was obtained.

As primers for amplifying a region from around the initiation codon of the rpsL gene to about 1500 bp upstream thereof, oligonucleotides consisting of the nucleotide sequences shown by SEQ ID NO:4 and 5, respectively, were synthesized; as primers for amplifying a region from around the stop codon of the rpsL gene to about 1500 bp downstream thereof, oligonucleotides consisting of the nucleotide sequences shown by SEQ ID NO:6 and 7, respectively, were synthesized.

The oligonucleotide consisting of the nucleotide sequence shown by SEQ ID NO:5 and the oligonucleotide consisting of the nucleotide sequence shown by SEQ ID NO:7 have been designed based on the sequence from the initiation codon to about 120 nucleotides; since they have the A at the 128th position from the initiation codon substituted by C, they have been designed to allow the K43T mutation to be introduced into the rpsL gene by ligating the amplification products obtained using the respective oligonucleotides as primers at this part.

As primers for amplifying a region from about 1200 bp upstream of the initiation codon of the rpsL gene to about 1200 bp downstream of the stop codon, oligonucleotides consisting of the nucleotide sequences shown by SEQ ID NO:8 and 9, respectively, were synthesized.

Using the oligonucleotides consisting of the nucleotide sequences shown by SEQ ID NO:4 and 5, and the oligonucleotides consisting of the nucleotide sequences shown by SEQ ID NO:6 and 7, as primer sets, respectively, with the genomic DNA of the *Escherichia coli* W3110 strain prepared by a conventional method as the template, a first PCR was performed, whereby amplification products were obtained.

The amplification products, each purified using the Qiaquick PCR purification Kit (produced by QIAGEN), were mixed in an equal molar ratio; with this as the template, and using the oligonucleotides consisting of the nucleotide sequences shown by SEQ ID NO:8 and 9, respectively, as a primer set, a second PCR was performed, whereby an amplification product was obtained.

The reaction mixture was subjected to agarose gel electrophoresis, and an about 2.5-kb amplified DNA fragment was separated using the Qiaquick Gel Extraction Kit (produced by QIAGEN), whereby a DNA fragment comprising the rpsL gene including the streptomycin resistance mutation K43T and a region therearound was obtained.

Next, the plasmid pKD46 comprising the gene that encodes λ recombinase was introduced into the *Escherichia coli* W3110 strain. The W3110 strain containing pKD46 was cultured according to a reference document [Datsenko, K. A., Warner, B. L., Proceedings of the National Academy of Science of the United States of America, Vol. 97. 6640-6645 (2000)] to prepare competent cells, and the DNA fragment comprising the rpsL gene including the streptomycin resistance mutation K43T and a region therearound, obtained above, was introduced by electroporation.

The transformant was applied to an LB agar plate containing 30 μg/ml streptomycin (LB+streptomycin) and cultured, and a streptomycin-resistant colony was selected. The colony selected was replica-plated to an LB agar plate containing 100 μg/ml ampicillin (LB+ampicillin) and cultured, and a colony exhibiting ampicillin sensitivity was selected from among the resulting colonies. The strain thus obtained was designated as the *Escherichia coli* RE1 strain.

(2) Deletion of the argR Gene
(a) Construction of Marker Genes for Gene Deletion The cat gene and the sacB gene to be used as marker genes for gene deletion and gene substitution in *Escherichia coli* using homologous recombination were isolated by the methods described below.

As primers for amplifying from about 200 bp upstream to about 100 bp downstream of the cat gene on the cloning vector pHSG396 (produced by Takara Bio Inc.), oligonucleotides consisting of the nucleotide sequences shown by SEQ ID NO:10 and 11, respectively, were synthesized; as primers for amplifying from about 300 bp upstream to about 100 bp downstream of the sacB gene of *Bacillus subtilis* 168 strain, oligonucleotides consisting of the nucleotide sequences shown by SEQ ID NO:12 and 13, respectively, were synthesized. A SalI recognition site was conferred to the oligonucleotides consisting of the nucleotide sequences shown by SEQ ID NO:10 and 12.

Using the oligonucleotides consisting of the nucleotide sequences shown by SEQ ID NO:10 and 11 as a primer set, with pHSG396 as the template, a PCR was performed, whereby a DNA fragment comprising the cat gene was obtained. The PCR was performed using KOD-Plus—(produced by Toyobo Co., Ltd.) according to the protocol attached thereto. Using the oligonucleotides consisting of the nucleotide sequences shown by SEQ ID NO:12 and 13 as a primer set, with the genomic DNA of the wild-type of *Bacillus subtilis* 168 strain prepared by a conventional method as the template, a PCR was performed, whereby a DNA fragment comprising the sacB gene was obtained.

The DNA fragment comprising the cat gene and the DNA fragment comprising the sacB gene were each purified, and then cleaved with SalI. Phenol/chloroform treatment and ethanol precipitation were performed, and the two cleavage products were mixed in an equal molar ratio and ligated using the DNA ligation Kit Ver. 2 (produced by Takara Bio Inc.). The ligation reaction mixture was purified by phenol-chloroform treatment and ethanol precipitation; with this as the template, and using the oligonucleotides consisting of the nucleotide sequences shown by SEQ ID NO:11 and 13 as a primer set, a PCR was performed; the amplified DNA obtained was purified to yield a DNA fragment comprising the cat gene and the sacB gene (cat-sacB fragment).

(b) Preparation of Strain Lacking the argR Gene

As primers for amplifying a region from around the initiation codon of the argR gene to about 1500 bp upstream thereof, oligonucleotides consisting of the nucleotide sequences shown by SEQ ID NO:14, 15 and 16, respectively, were synthesized; as primers for amplifying a region from around the stop codon of the argR gene to about 1500 bp downstream thereof, oligonucleotides consisting of the nucleotide sequences shown by SEQ ID NO:17, 18 and 19, respectively, were synthesized.

The oligonucleotide consisting of the nucleotide sequence shown by SEQ ID NO:15 has a sequence complementary to the nucleotide sequence shown by SEQ ID NO:11 as a part thereof, and the oligonucleotide consisting of the nucleotide sequence shown by SEQ ID NO:18 has a sequence complementary to the nucleotide sequence shown by SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:16 and the oligonucleotide consisting of the nucleotide sequence shown by SEQ ID NO:19 have a mutually complementary sequence in a part thereof, and have been designed to allow the argR gene to be deleted by ligating the amplification products obtained using the respective oligonucleotides as primers at this part.

As primers for amplifying from about 1200 bp upstream of the initiation codon of the argR gene to about 1200 bp downstream of the stop codon, oligonucleotides consisting of the nucleotide sequences shown by SEQ ID NO:20 and 21, respectively, were synthesized.

Using the oligonucleotides consisting of the nucleotide sequences shown by SEQ ID NO:14 and 15 and the oligonucleotides consisting of the nucleotide sequences shown by SEQ ID NO:17 and 18 as primer sets, respectively, with the genomic DNA of the *Escherichia coli* W3110 strain prepared by a conventional method as the template, a first PCR was performed, whereby amplification products were obtained.

The amplification products, purified using the Qiaquick PCR purification Kit, and the cat-sacB fragment were mixed in an equal molar ratio; with this as the template, and using the oligonucleotides consisting of the nucleotide sequences shown by SEQ ID NO:20 and 21, respectively, as a primer set, a second PCR was performed, whereby an amplification product was obtained.

The reaction mixture was subjected to agarose gel electrophoresis, and an about 6-kb DNA fragment was separated using the Qiaquick Gel Extraction Kit, whereby a DNA fragment comprising a region around argR having the cat-sacB fragment inserted therein was obtained.

Using the oligonucleotides consisting of the nucleotide sequences shown by SEQ ID NO:14 and 16 and the oligonucleotides consisting of the nucleotide sequences shown by SEQ ID NO:17 and 19 as primer sets, respectively, with the genomic DNA of W3110 strain as the template, a first PCR was performed, whereby amplification products were obtained.

The amplification products, each purified using the Qiaquick PCR purification Kit, were mixed in an equal molar ratio; with this as the template, and using the oligonucleotides consisting of the nucleotide sequences shown by SEQ ID NO:20 and 21 as a primer set, a second PCR was performed, whereby an amplification product was obtained.

The reaction mixture was subjected to agarose gel electrophoresis, and an about 2.5-kb DNA fragment was separated using the Qiaquick Gel Extraction Kit, whereby a DNA fragment comprising a region around argR lacking the argR gene was obtained.

Next, the plasmid pKD46 comprising the gene that encodes λ recombinase was introduced into the *Escherichia coli* RE1 strain to acquire an *Escherichia coli* RE1 strain containing pKD46. The transformant strain obtained was cultured according to the method of (1) above to prepare competent cells, and the DNA fragment comprising a region around argR including the cat-sacB fragment, obtained above, was introduced by electroporation.

The transformant obtained was spread on an LB agar plate containing 25 μg/ml chloramphenicol (LB+chloramphenicol) and cultured, and a chloramphenicol-resistant colony was selected. Since the strain undergoing homologous recombination exhibits chloramphenicol resistance and sucrose sensitivity, the colony selected was replica-plated to an LB agar plate containing 6% sucrose (LB+sucrose) and an LB+chloramphenicol plate, and a strain exhibiting both chloramphenicol resistance and sucrose sensitivity was selected.

On the strain selected, a colony PCR was performed using the oligonucleotides consisting of the nucleotide sequences shown by SEQ ID NO:14 and 17 as a primer set, and the insertion of the cat-sacB fragment at the position of the argR gene was confirmed. The strain including the cat-sacB fragment at the position of the argR gene was cultured as described above to prepare competent cells, and the DNA fragment comprising a region around argR lacking the argR gene, obtained above, was introduced by electroporation.

The transformant obtained was cultured using an LB+sucrose plate, and a sucrose-resistant colony was selected. Since the strain that has undergone homologous recombination does not comprise the cat-sacB fragment, and hence exhibits both chloramphenicol sensitivity and sucrose resistance, the colony selected was replica-plated to an LB+chloramphenicol plate and an LB+sucrose plate, and strains exhibiting both chloramphenicol sensitivity and sucrose resistance were selected.

From among the strains selected, a strain exhibiting ampicillin sensitivity, that is, a strain from which pKD46 had dropped, was selected, on which strain using the oligonucleotides consisting of the nucleotide sequences shown by SEQ ID NO:14 and 17 as a primer set, a colony PCR was performed, whereby the lack of the argR gene was confirmed.

As described above, a strain lacking the argR gene was obtained, which was designated as the *Escherichia coli* RE2 strain.

(3) Preparation of Strain Lacking the argK Gene

As primers for amplifying a region from around the initiation codon of the argK gene to about 1500 bp upstream thereof, oligonucleotides consisting of the nucleotide sequences shown by SEQ ID NO:22, 23 and 24, respectively, were synthesized; as primers for amplifying a region from around the stop codon of the argK gene to about 1500 bp downstream thereof, oligonucleotides consisting of the nucleotide sequences shown by SEQ ID NO:25, 26 and 27, respectively, were synthesized.

The oligonucleotide consisting of the nucleotide sequence shown by SEQ ID NO:23 has a sequence complementary to the nucleotide sequence shown by SEQ ID NO:11 as a part thereof; the oligonucleotide consisting of the nucleotide sequence shown by SEQ ID NO:26 has a sequence complementary to the oligonucleotide consisting of the nucleotide sequence shown by SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:24 and the oligonucleotide consisting of the nucleotide sequence shown by SEQ ID NO:27 have a mutually complementary sequence in a part thereof, and have been designed to allows the argK gene to be deleted by ligating the amplification products obtained using the respective oligonucleotides as primers at this part.

As primers for amplifying a region from about 1200 bp upstream of the initiation codon of the argK gene to about 1200 bp downstream of the stop codon, oligonucleotides consisting of the nucleotide sequences shown by SEQ ID NO:28 and 29, respectively, were synthesized.

Using the oligonucleotides consisting of the nucleotide sequences shown by SEQ ID NO:22 and 23 and the oligonucleotides consisting of the nucleotide sequences shown by SEQ ID NO:25 and 26 as primer sets, respectively, with the genomic DNA of the *Escherichia coli* W3110 strain prepared by a conventional method as the template, a first PCR was performed, whereby amplification products were obtained.

The amplification products, purified using the Qiaquick PCR purification Kit, and the cat-sacB fragment were mixed in an equal molar ratio; with this as the template, and using the oligonucleotides consisting of the nucleotide sequences shown by SEQ ID NO:28 and 29 as a primer set, a second PCR was performed, whereby an amplification product was obtained.

The reaction mixture was subjected to agarose gel electrophoresis, and an about 6-kb DNA fragment was separated using the Qiaquick Gel Extraction Kit, whereby a DNA fragment comprising a region around argK having the cat-sacB fragment inserted therein was obtained.

Using the oligonucleotides consisting of the nucleotide sequences shown by SEQ ID NO:22 and 24 and the oligonucleotides consisting of the nucleotide sequences shown by SEQ ID NO:25 and 27 as primer sets, respectively, with the genomic DNA of the *Escherichia coli* W3110 strain as the template, a first PCR was performed, whereby amplified fragments were obtained.

The amplification products, each purified using the Qiaquick PCR purification Kit, were mixed in an equal molar ratio; with this as the template, and using the oligonucleotides consisting of the nucleotide sequences shown by SEQ ID NO:28 and 29 as a primer set, a second PCR was performed, whereby an amplified fragment was obtained. The reaction mixture was subjected to agarose gel electrophoresis, and an about 2.5-kb DNA fragment was separated using the Qiaquick Gel Extraction Kit, whereby a DNA fragment comprising a region around argK lacking the argK gene was obtained.

Next, a strain lacking the argK gene was obtained using the DNA fragment obtained above and the strain obtained by introducing pKD46 into the *Escherichia coli* RE2 strain, by a method according to (2)(b) above, which was designated as the *Escherichia coli* RE3 strain.

(4) Preparation of Strain Lacking the astA Gene

As primers for amplifying a region from around the initiation codon of the astA gene to about 1500 bp upstream thereof, oligonucleotides consisting of the nucleotide sequences shown by SEQ ID NO:30, 31 and 32, respectively, were synthesized; as primers for amplifying a region from around the stop codon of the astA gene to about 1500 bp downstream thereof, oligonucleotides consisting of the nucleotide sequences shown by SEQ ID NO:33, 34 and 35, respectively, were synthesized.

The oligonucleotide consisting of the nucleotide sequence shown by SEQ ID NO:31 has a sequence complementary to the nucleotide sequence shown by SEQ ID NO:11 as a part thereof; the oligonucleotide consisting of the nucleotide sequence shown by SEQ ID NO:34 has a sequence complementary to the nucleotide sequence shown by SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:32 and the oligonucleotide consisting of the nucleotide sequence shown by SEQ ID NO:35 have a mutually complementary sequence in a part thereof, and have been designed to allow the astA gene to be deleted by ligating the amplification products obtained using the respective oligonucleotides as primers at this part.

As primers for amplifying a region from about 1200 bp upstream of the initiation codon of the astA gene to about 1200 bp downstream of the stop codon, oligonucleotides consisting of the nucleotide sequences shown by SEQ ID NO:36 and 37, respectively, were synthesized.

Using the oligonucleotides consisting of the nucleotide sequences shown by SEQ ID NO:30 and 31 and the oligonucleotides consisting of the nucleotide sequences shown by SEQ ID NO:33 and 34 as primer sets, respectively, with the genomic DNA of the *Escherichia coli* W3110 strain prepared by a conventional method as the template, a first PCR was performed, whereby amplified fragments were obtained.

The amplification products, purified using the Qiaquick PCR purification Kit, and the cat-sacB fragment were mixed in an equal molar ratio; with this as the template, and using the oligonucleotides consisting of the nucleotide sequences shown by SEQ ID NO:36 and 37 as a primer set, a second PCR was performed, whereby an amplified fragment was obtained.

The reaction mixture was subjected to agarose gel electrophoresis, and an about 6-kb DNA fragment was separated using the Qiaquick Gel Extraction Kit, whereby a DNA fragment comprising a region around astA having the cat-sacB fragment inserted therein was obtained.

Using the oligonucleotides consisting of the nucleotide sequences shown by SEQ ID NO:30 and 32 and the oligonucleotides consisting of the nucleotide sequences shown by SEQ ID NO:33 and 35 as primer sets, respectively, with the genomic DNA of the *Escherichia coli* W3110 strain as the template, a first PCR was performed, whereby amplified fragments were obtained.

The amplification products, each purified using the Qiaquick PCR purification Kit, were mixed in an equal molar ratio; with this as the template, and using the oligonucleotides consisting of the nucleotide sequences shown by SEQ ID NO:36 and 37 as a primer set, a second PCR was performed, whereby an amplification product was obtained.

The reaction mixture was subjected to agarose gel electrophoresis, and an about 2.5-kb DNA fragment was separated using the Qiaquick Gel Extraction Kit, whereby a DNA fragment comprising a region around astA lacking the astA gene was obtained.

Next, a strain lacking the astA gene from the *Escherichia coli* RE3 strain was obtained using the DNA fragment obtained above and the strain obtained by introducing pKD46 into the *Escherichia coli* RE3 strain, by a method according to (2)(b) above, which was designated as the *Escherichia coli* RE4 strain.

(5) Preparation of Strain Lacking the speAB Gene

As primers for amplifying a region from around the initiation codon of speA gene to about 1500 bp upstream thereof, oligonucleotides consisting of the nucleotide sequences shown by SEQ ID NO:38, 39 and 40, respectively, were synthesized; as primers for amplifying a region from around the stop codon of the speB gene to about 1500 bp downstream thereof, oligonucleotides consisting of the nucleotide sequences shown by SEQ ID NO:41, 42 and 43, respectively, were synthesized.

The oligonucleotide consisting of the nucleotide sequence shown by SEQ ID NO:39 has a sequence complementary to the nucleotide sequence shown by SEQ ID NO:11 as a part thereof; the oligonucleotide consisting of the nucleotide sequence shown by SEQ ID NO:42 has a sequence complementary to the nucleotide sequence shown by SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:40 and the oligonucleotide consisting of the nucleotide sequence shown by SEQ ID NO:43 have a mutually complementary sequence in a part thereof, and have been designed to allow the speA gene and the speB gene to be deleted by ligating the amplification products obtained using the respective oligonucleotides as primers at this part.

As primers for amplifying a region from about 1200 bp upstream of the initiation codon of the speA gene to about 1200 bp downstream of the stop codon of the speB gene, oligonucleotides consisting of the nucleotide sequences shown by SEQ ID NO:44 and 45, respectively, were synthesized.

Using the oligonucleotides consisting of the nucleotide sequences shown by SEQ ID NO:38 and 39 and the oligonucleotides consisting of the nucleotide sequences shown by SEQ ID NO:41 and 42 as primer sets, respectively, with the genomic DNA of the *Escherichia coli* W3110 strain prepared by a conventional method as the template, a first PCR was performed, whereby amplification products were obtained.

The amplification products, each purified using the Qiaquick PCR purification Kit, and the cat-sacB fragment were mixed in an equal molar ratio; with this as the template, and using the oligonucleotides consisting of the nucleotide sequences shown by SEQ ID NO:44 and 45 as a primer set, a second PCR was performed, whereby an amplification product was obtained.

The reaction mixture was subjected to agarose gel electrophoresis, and an about 6-kb DNA fragment was separated using the Qiaquick Gel Extraction Kit, whereby a DNA fragment comprising a region around speAB having the cat-sacB fragment inserted therein was obtained.

Using the oligonucleotides consisting of the nucleotide sequences shown by SEQ ID NO:38 and 40 and the oligonucleotides consisting of the nucleotide sequences shown by SEQ ID NO:41 and 43 as primer sets, respectively, with the genomic DNA of the *Escherichia coli* W3110 strain as the template, a first PCR was performed, whereby amplification products were obtained.

The amplification products, each purified using the Qiaquick PCR purification Kit, were mixed in an equal molar ratio; with this as the template, and using the oligonucleotides consisting of the nucleotide sequences shown by SEQ ID NO:44 and 45 as a primer set, a second PCR was performed, whereby an amplification product was obtained.

The reaction mixture was subjected to agarose gel electrophoresis, and an about 2.5-kb DNA fragment was separated using the Qiaquick Gel Extraction Kit, whereby a DNA fragment comprising a region around speAB lacking the speA gene and the speB gene was obtained.

Next, a strain lacking the speAB gene from the *Escherichia coli* RE4 strain was obtained using the DNA fragment obtained above and the strain obtained by introducing pKD46 into the *Escherichia coli* RE4 strain, by a method according to (2)(b) above, which was designated as the *Escherichia coli* RE5 strain.

(6) Preparation of Strain Lacking the Oat Gene

As primers for amplifying a region from around the initiation codon of the oat gene (also called the ygjG gene) to about 1500 bp upstream thereof, oligonucleotides consisting of the nucleotide sequences shown by SEQ ID NO:46, 47 and 48, respectively, were synthesized; as primers for amplifying a region from around the stop codon of the oat gene to about 1500 bp downstream thereof, oligonucleotides consisting of the nucleotide sequences shown by SEQ ID NO:49, 50 and 51, respectively, were synthesized.

The oligonucleotide consisting of the nucleotide sequence shown by SEQ ID NO:47 has a sequence complementary to the nucleotide sequence shown by SEQ ID NO:11 as a part thereof; the oligonucleotide consisting of the nucleotide sequence shown by SEQ ID NO:50 has a sequence complementary to the nucleotide sequence shown by SEQ ID NO:13 as a part thereof; these have been designed to allow the amplification products obtained using the respective oligonucleotide as primers to be ligated in a form between which the cat-sacB fragment, a marker gene, is sandwiched.

The oligonucleotide consisting of the nucleotide sequence shown by SEQ ID NO:48 and the oligonucleotide consisting of the nucleotide sequence shown by SEQ ID NO:51 have a mutually complementary sequence in a part thereof, and have been designed to allow the oat gene to be deleted by ligating the amplification products obtained using the respective oligonucleotides as primers at this part.

As primers for amplifying a region from about 1200 bp upstream of the initiation codon of the oat gene to about 1200 bp downstream of the stop codon, oligonucleotides consisting of the nucleotide sequences shown by SEQ ID NO:52 and 53, respectively, were synthesized.

Using the oligonucleotides consisting of the nucleotide sequences shown by SEQ ID NO:46 and 47 and the oligonucleotides consisting of the nucleotide sequences shown by SEQ ID NO:49 and 50 as primer sets, respectively, with the genomic DNA of the *Escherichia coli* W3110 strain prepared by a conventional method as the template, a first PCR was performed, whereby amplification products were obtained.

The amplification products, each purified using the Qiaquick PCR purification Kit, and the cat-sacB fragment were mixed in an equal molar ratio; with this as the template, and using the oligonucleotides consisting of the nucleotide sequences shown by SEQ ID NO:52 and 53 as a primer set, a second PCR was performed, whereby an amplification product was obtained.

The reaction mixture was subjected to agarose gel electrophoresis, and an about 6-kb DNA fragment was separated using the Qiaquick Gel Extraction Kit, whereby a DNA fragment comprising a region around the oat gene having the cat-sacB fragment inserted therein was obtained.

Using the oligonucleotides consisting of the nucleotide sequences shown by SEQ ID NO:46 and 48 and the oligonucleotides consisting of the nucleotide sequences shown by SEQ ID NO:49 and 51 as primer sets, respectively, with the genomic DNA of the *Escherichia coli* W3110 strain as the template, a first PCR was performed, whereby amplification products were obtained.

The amplification products, each purified using the Qiaquick PCR purification Kit, were mixed in an equal molar ratio; with this as the template, and using the oligonucleotides consisting of the nucleotide sequences shown by SEQ ID NO:52 and 53 as a primer set, a second PCR was performed, whereby an amplification product was obtained.

The reaction mixture was subjected to agarose gel electrophoresis, and an about 2.5-kb DNA fragment was separated using the Qiaquick Gel Extraction Kit, whereby a DNA fragment comprising a region around the oat gene lacking the oat gene was obtained.

Next, a strain lacking the oat gene from the *Escherichia coli* RE5 strain was obtained using the DNA fragment obtained above and the strain obtained by introducing pKD46 into the *Escherichia coli* RE5 strain, by a method according to (2)(b) above, which was designated as the *Escherichia coli* RE6 strain.

(7) Introduction of argA Desensitization Mutation

The Y19C mutation, reported to be a desensitization mutation in the argA gene, was introduced into chromosomal DNA by the method described below.

As primers for amplifying a region from around the initiation codon of the argA gene to about 1500 bp upstream thereof, oligonucleotides consisting of the nucleotide sequences shown by SEQ ID NO:54, 55 and 56, respectively, were synthesized; as primers for amplifying a region from around the initiation codon of the argA gene to about 1500 bp downstream thereof, oligonucleotides consisting of the nucleotide sequences shown by SEQ ID NO:57, 58 and 59, respectively, were synthesized.

The oligonucleotide consisting of the nucleotide sequence shown by SEQ ID NO:55 has a sequence complementary to the nucleotide sequence shown by SEQ ID NO:11 as a part thereof; the oligonucleotide consisting of the nucleotide sequence shown by SEQ ID NO:58 has a sequence complementary to the nucleotide sequence shown by SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:56 and the oligonucleotide consisting of the nucleotide sequence shown by SEQ ID NO:59 have been designed on the basis of a sequence from the initiation codon to about 50 nucleotides; since they have the A at the 56th position from the initiation codon substituted by G, they have been designed to allow the Y19C mutation to be introduced into the argA gene by ligating the amplification products obtained using the respective oligonucleotides as primers at this part.

As primers for amplifying a region from about 1200 bp upstream of the initiation codon of the argA gene to about 1200 bp downstream of the stop codon, oligonucleotides consisting of the nucleotide sequences shown by SEQ ID NO:60 and 61, respectively, were synthesized. Using the oligonucleotides consisting of the nucleotide sequences shown by SEQ ID NO:54 and 55 and the oligonucleotides consisting of the nucleotide sequences shown by SEQ ID NO:57 and 58 as primer sets, with the genomic DNA of the *Escherichia coli* W3110 strain prepared by a conventional method as the template, a first PCR was performed, whereby amplification products were obtained.

The amplification products, each purified using the Qiaquick PCR purification Kit, and the cat-sacB fragment were mixed in an equal molar ratio; with this as the template, and using the oligonucleotides consisting of the nucleotide sequences shown by SEQ ID NO:60 and 61 as a primer set, a second PCR was performed, whereby an amplification product was obtained.

The reaction mixture was subjected to agarose gel electrophoresis, and an about 6-kb amplified DNA fragment was separated using the Qiaquick Gel Extraction Kit (produced by QIAGEN), whereby a DNA fragment comprising a region around argA having the cat-sacB fragment inserted therein was obtained.

Using the oligonucleotides consisting of the nucleotide sequences shown by SEQ ID NO:54 and 56 and the oligonucleotides consisting of the nucleotide sequences shown by SEQ ID NO:57 and 59 as primer sets, respectively, with the genomic DNA of the *Escherichia coli* W3110 strain as the template, a first PCR was performed, whereby amplification products were obtained.

The amplification products, purified using the Qiaquick PCR purification Kit, were mixed in an equal molar ratio; with this as the template, and using the oligonucleotides consisting of the nucleotide sequences shown by SEQ ID NO:60 and 61 as a primer set, a second PCR was performed, whereby an amplification product was obtained.

The reaction mixture was subjected to agarose gel electrophoresis, and an about 2.5-kb DNA fragment was separated using the Qiaquick Gel Extraction Kit, whereby a DNA fragment, comprising the argA gene including the desensitization mutation Y19C and a region therearound, was obtained. Next, a strain including the desensitization mutation Y19C introduced into the argA gene of the *Escherichia coli* RE6 strain was obtained using the DNA fragment obtained above and the strain obtained by introducing pKD46 into the *Escherichia coli* RE6 strain, by a method according to (2)(b) above, which was designated as the *Escherichia coli* RE7 strain.

EXAMPLE 2

Preparation of Strain Lacking the csrB Gene and Strain Lacking the csrC Gene (1) Preparation of Strain Lacking the csrB Gene As primers for amplifying a region from about 100 bp upstream of the 5' end of the transcription region of the csrB gene to about 1600 bp upstream thereof, oligonucleotides consisting of the nucleotide sequences shown by SEQ ID NO:62, 63 and 64, respectively, were synthesized; as primers for amplifying a region from about 20 bp downstream of the 3' end of the transcription region of the csrB gene to about 1500 bp downstream thereof, oligonucleotides consisting of the nucleotide sequences shown by SEQ ID NO:65, 66 and 67, respectively, were synthesized.

The oligonucleotide consisting of the nucleotide sequence shown by SEQ ID NO:63 has a sequence complementary to the primer of SEQ ID NO:11 as a part thereof; the oligonucleotide consisting of the nucleotide sequence shown by SEQ ID NO:66 has a sequence complementary to the primer of SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:64 and the oligonucleotide consisting of the nucleotide sequence shown by SEQ ID NO:67 have a mutually complementary sequence in a part thereof, and have been designed to allow the transcription region of the csrB gene to be deleted by ligating the amplification products obtained using the respective oligonucleotides as primers at this part.

As primers for amplifying a region from about 1300 bp upstream of the 5' end of the transcription region of the csrB gene to about 1200 bp downstream of the 3' end, oligonucleotides consisting of the nucleotide sequences shown by SEQ ID NO:68 and 69, respectively, were synthesized.

Using the oligonucleotides consisting of the nucleotide sequences shown by SEQ ID NO:62 and 63 and the oligonucleotides consisting of the nucleotide sequences shown by SEQ ID NO:65 and 66 as primer sets, respectively, with the genomic DNA of the *Escherichia coli* W3110 strain prepared by a conventional method as the template, a first PCR was performed, whereby amplification products were obtained.

The amplification products, purified using the Qiaquick PCR purification Kit, and the cat-sacB fragment were mixed in an equal molar ratio; with this as the template, and using the oligonucleotides consisting of the nucleotide sequences shown by SEQ ID NO:68 and 69 as a primer set, a second PCR was performed, whereby an amplification product was obtained.

The reaction mixture was subjected to agarose gel electrophoresis, and an about 6-kb DNA fragment was separated using the Qiaquick Gel Extraction Kit, whereby a DNA fragment comprising a region around csrB having the cat-sacB fragment inserted therein was obtained.

Using the oligonucleotides consisting of the nucleotide sequences shown by SEQ ID NO:62 and 64 and the oligonucleotides consisting of the nucleotide sequences shown by SEQ ID NO:65 and 67 as primer sets, respectively, with the genomic DNA of the *Escherichia coli* W3110 strain as the template, a first PCR was performed, whereby amplification products were obtained.

The amplification products, purified using the Qiaquick PCR purification Kit, were mixed in an equal molar ratio; with this as the template, and using the oligonucleotides consisting of the nucleotide sequences shown by SEQ ID NO:68 and 69 as a primer set, a second PCR was performed, whereby an amplification product was obtained.

The reaction mixture was subjected to agarose gel electrophoresis, and an about 2.5-kb DNA fragment was separated using the Qiaquick Gel Extraction Kit, whereby a DNA fragment comprising a region around csrB lacking the csrB gene was obtained.

Next, a strain lacking the csrB gene from the *Escherichia coli* RE7 strain was obtained using the DNA fragment obtained above and the strain obtained by introducing pKD46 into the *Escherichia coli* RE7 strain, by a method according to (2)(b) above, which was designated as the *Escherichia coli* RE7ΔcsrB strain.

(2) Preparation of Strain Lacking the csrC Gene

As primers for amplifying a region from about 200 bp upstream of the 5' end of the transcription region of the csrC gene to about 1600 bp upstream thereof, oligonucleotides consisting of the nucleotide sequences shown by SEQ ID NO:70, 71 and 72, respectively, were synthesized; as primers for amplifying a region from about 20 bp downstream of the 3' end of the transcription region of the csrC gene to about 1500 bp downstream thereof, oligonucleotides consisting of the nucleotide sequences shown by SEQ ID NO:73, 74 and 75, respectively, were synthesized.

The oligonucleotide consisting of the nucleotide sequence shown by SEQ ID NO:71 has a sequence complementary to the oligonucleotide consisting of the nucleotide sequence shown by SEQ ID NO:11 as a part thereof; the oligonucleotide consisting of the nucleotide sequence shown by SEQ ID NO:74 has a sequence complementary to the oligonucleotide consisting of the nucleotide sequence shown by SEQ ID NO:13 as a part thereof; these have been designed to allow the amplification products obtained using the respective oligonucleotides as primers to be ligated in a form between which the cat-sacB fragment, a marker gene, is sandwiched.

The oligonucleotide consisting of the nucleotide sequence shown by SEQ ID NO:72 and the oligonucleotide consisting of the nucleotide sequence shown by SEQ ID NO:75 have a mutually complementary sequence in a part thereof, and have been designed to allow the transcription regions of the csrC gene to be deleted by ligating the amplification products obtained using the respective oligonucleotides as primers at this part.

As primers for amplifying a region from about 1500 bp upstream of the 5' end of the transcription region of the csrC gene to about 1300 bp downstream of the 3' end, oligonucleotides consisting of the nucleotide sequences shown by SEQ ID NO:76 and 77, respectively, were synthesized.

Using the oligonucleotides consisting of the nucleotide sequences shown by SEQ ID NO:70 and 71 and the oligonucleotides consisting of the nucleotide sequences shown by SEQ ID NO:73 and 74 as primer sets, respectively, with the genomic DNA of the *Escherichia coli* W3110 strain prepared by a conventional method as the template, a first PCR was performed, whereby amplification products were obtained.

The amplification products, each purified using the Qiaquick PCR purification Kit, and the cat-sacB fragment were mixed in an equal molar ratio; with this as the template, and using the oligonucleotides consisting of the nucleotide sequences shown by SEQ ID NO:76 and 77 as a primer set, a second PCR was performed, whereby an amplification product was obtained.

The reaction mixture was subjected to agarose gel electrophoresis, and an about 6-kb DNA fragment was separated using the Qiaquick Gel Extraction Kit, whereby a DNA fragment comprising a region around csrC having the cat-sacB fragment inserted therein was obtained.

Using the oligonucleotides consisting of the nucleotide sequences shown by SEQ ID NO:70 and 72 and the oligonucleotides consisting of the nucleotide sequences shown by SEQ ID NO:73 and 75 as primer sets, respectively, with the genomic DNA of the *Escherichia coli* W3110 strain as the template, a first PCR was performed, whereby amplification products were obtained.

The amplification products, each purified using the Qiaquick PCR purification Kit, were mixed in an equal molar ratio; with this as the template, and using the oligonucleotides consisting of the nucleotide sequences shown by SEQ ID NO:76 and 77 as primer sets, respectively, a second PCR was performed, whereby amplification products were obtained.

The reaction mixture was subjected to agarose gel electrophoresis, and an about 2.5-kb DNA fragment was separated using the Qiaquick Gel Extraction Kit, whereby a DNA fragment comprising a region around csrC lacking the csrC gene was obtained.

Next, a strain lacking the csrC gene from the *Escherichia coli* RE7 strain was obtained using the DNA fragment obtained above and the strain obtained by introducing pKD46 into the *Escherichia coli* RE7 strain, by a method according to (2)(b) above, which was designated as the *Escherichia coli* RE7ΔcsrC strain.

EXAMPLE 3

Production of Amino Acids Using Strain Lacking the csrB Gene and Strain Lacking the csrC Gene (1) Culturing of Strain Lacking the csrB Gene and Strain Lacking the csrC Gene The *Escherichia coli* RE7 strain, the *Escherichia coli* RE7ΔcsrB strain, and the *Escherichia coli* RE7ΔcsrC strain were each cultured on an LB+streptomycin plate at 30° C. overnight, and each was inoculated to a baffled 2-L conical flask containing 300 ml of a medium consisting of glucose 15 g/L, soybean peptone 10 g/L, yeast extract 10 g/L, NaCl 2.5 g/L, and $CaCO_3$ 30 g/L, and cultured at 30° C. for 24 hours.

After completion of the culturing, 50 ml of the culture was inoculated to a jar fermenter containing 800 ml of a seed medium [glucose 30 g/L, yeast extract 2 g/L, $(NH_4)_2SO_4$ 15 g/L, $KH_2PO_4$ 5 g/L, $MgSO_4.7H_2O$ 1.8 g/L, NaCl 0.6 g/L, $CaCl_2.2H_2O$ 0.2 g/L, $FeSO_4.7H_2O$ 50 mg/L, $ZnSO_4.7H_2O$ 12 mg/L, $MnSO_4.7H_2O$ 5 mg/L, $CuSO_4.5H_2O$ 0.5 mg/L, thiamin hydrochloride 0.1 g/L], and cultured at 35° C. at an aeration rate of 1 L/min with stirring at 800 rpm. During the culturing, an 18% ammonia solution was added to maintain pH 6.8.

After the culturing was continued until the glucose was consumed completely, 38 ml of the culture was inoculated to a jar fermenter containing 450 ml of a fermentation medium [glucose 30 g/L (prepared by separate steaming), corn steep liquor 3 g/L, $(NH_4)_2SO_4$ 20 g/L, $KH_2PO_4$ 4.2 g/L, $MgSO_4 \cdot 7H_2O$ 2.5 g/L, $Na_2SO_4$ 0.7 g/L, $CaCl_2 \cdot 2H_2O$ 0.23 g/L, $FeSO_4 \cdot 7H_2O$ 20 mg/L, $MnSO_4 \cdot 7H_2O$ 10 mg/L, $ZnSO_4 \cdot 7H_2O$ 2 mg/L, $CuSO_4 \cdot 5H_2O$ 2 mg/L, $NiCl_2 \cdot 6H_2O$ 2 mg/L, $CoCl_2 \cdot 6H_2O$ 2 mg/L, β-alanine 50 mg/L, nicotinic acid 50 mg/L, thiamin hydrochloride 40 mg/L, biotin 490 μg/L], and cultured at 35° C. and an aeration rate of 2 L/min with stirring at 1200 rpm. During the culturing, an 18% ammonia solution was added to maintain pH 6.8.

Starting at the time when the glucose in the culture had been consumed completely, a feed medium [glucose 600 g/L, $(NH_4)_2SO_4$ 68 g/L (each prepared by separate steaming)] was fed at a rate of 17 ml/hour, and the culturing was continued until 425 ml of the feed medium had been added. After completion of the culturing, the L-arginine concentration in the culture supernatant was determined by HPLC.

HPLC analysis was performed at 60° C. using AQ-312 (produced by YMC Co., Ltd.) as the separation column and a pH 6.0 solution containing sodium citrate 2.94 g/L, sodium sulfate 1.42 g/L, acetonitrile 233 mL/L and sodium lauryl sulfate 3 g/L as the mobile phase. After mixing the eluate from the separation column and the reaction mixture (a solution containing boric acid 18.5 g/L, NaOH 11 g/L, ortho-phthalaldehyde 0.6 g/L, mercaptoethanol 2 ml/L and Brige-35 3 mL/L), amino acid detection and quantitation were achieved by fluorescent analysis at an excitation wavelength of 345 nm and an absorption wavelength of 455 nm. The results are shown in Table 1.

TABLE 1

| Strain | Amount of accumulated L-arginine | Yield (%) relative to sugar |
| --- | --- | --- |
| RE7 | 49.9 | 17.3 |
| RE7ΔcsrB | 70.3 | 25.8 |
| RE7ΔcsrC | 69.2 | 23.9 |

As shown in Table 1, both the strain lacking the csrB gene and the strain lacking the csrC gene exhibited an improvement in both the amount of L-arginine accumulated and percent yield relative to the sugar, compared with the parent strain.

INDUSTRIAL APPLICABILITY

According to the present invention, an L-amino acid can be produced industrially advantageously.

[Sequence Listing Free Text]

SEQ ID NO:1—explanation of artificial sequence: conserved sequence
SEQ ID NO:2—explanation of artificial sequence: conserved sequence
SEQ ID NO:3—explanation of artificial sequence: conserved sequence
SEQ ID NO:4—explanation of artificial sequence: synthetic DNA
SEQ ID NO:5—explanation of artificial sequence: synthetic DNA
SEQ ID NO:6—explanation of artificial sequence: synthetic DNA
SEQ ID NO:7—explanation of artificial sequence: synthetic DNA
SEQ ID NO:8—explanation of artificial sequence: synthetic DNA
SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:17—explanation of artificial sequence: synthetic DNA
SEQ ID NO:18—explanation of artificial sequence: synthetic DNA
SEQ ID NO:19—explanation of artificial sequence: synthetic DNA
SEQ ID NO:20—explanation of artificial sequence: synthetic DNA
SEQ ID NO:21—explanation of artificial sequence: synthetic DNA
SEQ ID NO:22—explanation of artificial sequence: synthetic DNA
SEQ ID NO:23—explanation of artificial sequence: synthetic DNA
SEQ ID NO:24—explanation of artificial sequence: synthetic DNA
SEQ ID NO:25—explanation of artificial sequence: synthetic DNA
SEQ ID NO:26—explanation of artificial sequence: synthetic DNA
SEQ ID NO:27—explanation of artificial sequence: synthetic DNA
SEQ ID NO:28—explanation of artificial sequence: synthetic DNA
SEQ ID NO:29—explanation of artificial sequence: synthetic DNA
SEQ ID NO:30—explanation of artificial sequence: synthetic DNA
SEQ ID NO:31—explanation of artificial sequence: synthetic DNA
SEQ ID NO:32—explanation of artificial sequence: synthetic DNA
SEQ ID NO:33—explanation of artificial sequence: synthetic DNA
SEQ ID NO:34—explanation of artificial sequence: synthetic DNA
SEQ ID NO:35—explanation of artificial sequence: synthetic DNA
SEQ ID NO:36—explanation of artificial sequence: synthetic DNA
SEQ ID NO:37—explanation of artificial sequence: synthetic DNA
SEQ ID NO:38—explanation of artificial sequence: synthetic DNA
SEQ ID NO:39—explanation of artificial sequence: synthetic DNA SEQ ID NO:40—explanation of artificial sequence: synthetic DNA
SEQ ID NO:41—explanation of artificial sequence: synthetic DNA
SEQ ID NO:42—explanation of artificial sequence: synthetic DNA
SEQ ID NO:43—explanation of artificial sequence: synthetic DNA
SEQ ID NO:44—explanation of artificial sequence: synthetic DNA
SEQ ID NO:45—explanation of artificial sequence: synthetic DNA
SEQ ID NO:46—explanation of artificial sequence: synthetic DNA
SEQ ID NO:47—explanation of artificial sequence: synthetic DNA
SEQ ID NO:48—explanation of artificial sequence: synthetic DNA
SEQ ID NO:49—explanation of artificial sequence: synthetic DNA
SEQ ID NO:50—explanation of artificial sequence: synthetic DNA
SEQ ID NO:51—explanation of artificial sequence: synthetic DNA
SEQ ID NO:52—explanation of artificial sequence: synthetic DNA
SEQ ID NO:53—explanation of artificial sequence: synthetic DNA
SEQ ID NO:54—explanation of artificial sequence: synthetic DNA
SEQ ID NO:55—explanation of artificial sequence: synthetic DNA
SEQ ID NO:56—explanation of artificial sequence: synthetic DNA
SEQ ID NO:57—explanation of artificial sequence: synthetic DNA
SEQ ID NO:58—explanation of artificial sequence: synthetic DNA
SEQ ID NO:59—explanation of artificial sequence: synthetic DNA
SEQ ID NO:60—explanation of artificial sequence: synthetic DNA
SEQ ID NO:61—explanation of artificial sequence: synthetic DNA
SEQ ID NO:62—explanation of artificial sequence: synthetic DNA
SEQ ID NO:63—explanation of artificial sequence: synthetic DNA
SEQ ID NO:64—explanation of artificial sequence: synthetic DNA
SEQ ID NO:65—explanation of artificial sequence: synthetic DNA
SEQ ID NO:66—explanation of artificial sequence: synthetic DNA
SEQ ID NO:67—explanation of artificial sequence: synthetic DNA
SEQ ID NO:68—explanation of artificial sequence: synthetic DNA
SEQ ID NO:69—explanation of artificial sequence: synthetic DNA
SEQ ID NO:70—explanation of artificial sequence: synthetic DNA
SEQ ID NO:71—explanation of artificial sequence: synthetic DNA
SEQ ID NO:72—explanation of artificial sequence: synthetic DNA
SEQ ID NO:73—explanation of artificial sequence: synthetic DNA
SEQ ID NO:74—explanation of artificial sequence: synthetic DNA
SEQ ID NO:75—explanation of artificial sequence: synthetic DNA
SEQ ID NO:76—explanation of artificial sequence: synthetic DNA
SEQ ID NO:77—explanation of artificial sequence: synthetic DNA

The invention claimed is:

1. A process for producing an amino acid, which method comprises culturing a modified *Escherichia coli* microorganism in a medium to produce and accumulate the amino acid in the medium, and recovering the amino acid from the medium, wherein the amino acid is selected from the group consisting of L-ornithine, L-citrulline, and L-arginine, and wherein the modified *Escherichia coli* microorganism has a loss of a function of a CsrC RNA resulting from modifying a parental *Escherichia coli* microorganism which has an ability to produce and accumulate the amino acid in the medium when the parental *Escherichia coli* microorganism is cultured in the medium, by a deletion, substitution, or addition in the nucleotide sequence of SEQ ID NO: 79 of the parental *Escherichia coli* microorganism.

2. The process of claim 1, wherein the modified microorganism comprises a deletion of the nucleotide sequence of SEQ ID NO: 79.

3. The process of claim 1, wherein the modified microorganism comprises a deletion in the nucleotide sequence of SEQ ID NO: 79.

4. The process of claim 1, wherein the modified microorganism comprises a substitution in the nucleotide sequence of SEQ ID NO: 79.

5. The process of claim 1, wherein the modified microorganism comprises an addition in the nucleotide sequence of SEQ ID NO: 79.

* * * * *

```
                             SEQUENCE LISTING

<160> NUMBER OF SEQ ID NOS: 79

<210> SEQ ID NO 1
<211> LENGTH: 7
<212> TYPE: DNA
<213> ORGANISM: Artificial Sequence
<220> FEATURE:
<223> OTHER INFORMATION: Description of Artificial Sequence: Conserved
      Sequence

<400> SEQUENCE: 1 caggatg                                                                  7

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence: Conserved
      Sequence

<400> SEQUENCE: 2 caggaag                                                                  7

<210> SEQ ID NO 3
```

-continued

```
<211> LENGTH: 7
<212> TYPE: DNA
<213> ORGANISM: Artificial Sequence
<220> FEATURE:
<223> OTHER INFORMATION: Description of Artificial Sequence: Conserved
      Sequence

<400> SEQUENCE: 3 caggacg                                                                    7

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
cggcgtatta atgaagtccc tgactatcgc                                          30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gcggagttcg gttttgtagg agtggtagta                                          30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
ttgaacgcag aaccacaggt taccaggatg                                          30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
actaccactc ctacaaaacc gaactccgc                                           29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gctggagttc accatcgaag aagtgaatgc                                          30

<210> SEQ ID NO 9
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      DNA

<400> SEQUENCE: 9
agttcaacca tgtctgccgg gatatcttcg                                          30

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
ggatttgcag actacgggcc taaagtcgac agaataaata aatcctggtg tccc              54

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gcggccgcac ttattcaggc gtagcac                                             27

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
gggacaccag gatttattta ttctgtcgac tttaggcccg tagtctgcaa atcc              54

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
gcggccgcat atcggcattt tcttttgcg                                           29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
tgcgtgatga taagcagtta acgctgcagg                                          30

<210> SEQ ID NO 15
<211> LENGTH: 49
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 15
gtgctacgcc tgaataagtg cggccgcatt gtcaaagcct tgctcctgc                49

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
aaccgttagc aggattgtca aagccttgct cctgc                               35

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
gacaggaccg gacgtgtact gcttaatcag                                     30

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
cgcaaaagaa aatgccgatt tgcggccgcc ctgctaacgg tttcacagtc               50

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
aggctttgac aatcctgcta acggtttcac agtc                                34

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
ggaatatccg gcaaccaatt aagtcgtgcg                                     30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA -continued

<400> SEQUENCE: 21
tttccgcgat gactaccaat gtggcacgtc                                              30

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
tacgctcgct gatgggattg agtac                                                   25

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gtgctacgcc tgaataagtg cggccgcagc tgcgtactta gtgcctgatg                        50

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
ttcttcggtc tgcagctgcg tacttagtgc ctgatgacg                                    39

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
cgcggatcgt gatagtgatt gagttc                                                  26

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
cgcaaaagaa aatgccgatt tgcggccgcg cagaccgaag aagaagtact g                      51

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27

```
taagtacgca gctgcagacc gaagaagaag tactgaatc                            39

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
atcaaagcag caatctctgc cggac                                           25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
ccgatgcttc aatgacggca acatc                                           25

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
atttccagtt agcctccgcc gtttatgcac                                      30

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
gtgctacgcc tgaataagtg cggccgccac gaacacatag ccctgctcac                50

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
tgagggcatc cagcacgaac acatagccct gctcac                               36

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
gaaaacggtg acgggtagag gcttcattac                                      30
```

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
cgcaaaagaa aatgccgatt tgcggccgcc tggatgccct caaatgccac            50

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
ctatgtgttc gtgctggatg ccctcaaatg ccacgc                           36

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
ggcacgaacc ctgcaatcta catttacagc                                  30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
ccgtcgaaat tgacttccca ggcgttcatc                                  30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
tacgaccagt cagaccgcag tcacccattg                                  30

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
gtgctacgcc tgaataagtg cggccgccca gctcgttaac gtcatagtag            50

```
<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
tacgtccatc ccaccagctc gttaacgtca tagtag                              36

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
tttcagttct tccatcggca gatcgtaacc                                     30

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
cgcaaaagaa aatgccgatt tgcggccgct gggatggacg tagtggaagt               50

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
gttaacgagc tggtgggatg gacgtagtgg aagtgg                              36

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
ttcttgcagc gatttctggt cgatctcttc                                     30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
ccaggacgga ttctgcgggt tgtgtttcag                                     30

<210> SEQ ID NO 46
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
cgatatcgtc cattgtcttg atcaccgtgg                                        30

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
gtgctacgcc tgaataagtg cggccgctca atcacctctc ggttaagtgc                  50

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
cagtggcggt tcatcaatca cctctcggtt aagtgc                                 36

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
ggttaacgcc ctgacttccc atcatctcgg                                        30

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
cgcaaaagaa aatgccgatt tgcggccgct gaaccgccac tgacactgac                  50

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
gagaggtgat tgatgaaccg ccactgacac tgacca                                 36

<210> SEQ ID NO 52
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 52
agagttctgt ttcaccgacg ccgccatttg                                          30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
tgggatgttc aggcctcgtt catgaattgc                                          30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
gcaagaatag actccgcaac ttcctgctgg                                          30

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
gtgctacgcc tgaataagtg cggccgcaat ggcggaatcc ctcgaccaac                    50

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
gtgggtattg atacagggaa ccgaatggcg                                          30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
tatgatgtcg agactgatcg acgccttgcc                                          30

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
```

DNA

<400> SEQUENCE: 58
cgcaaaagaa aatgccgatt tgcggccgca gcaaggtatt ctggtacgcc            50

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
cattcggttc cctgtatcaa tacccaccgg                                  30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
gctcttcctc aacgttactg ataaacgccg                                  30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
gatctttctc ggcgatcgtg atcaactggc                                  30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
acctttcaca accttctgcg tgaatccagc                                  30

<210> SEQ ID NO 63
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
gtgctacgcc tgaataagtg cggccgctcg cttatttcct ggcgatctcc            50

<210> SEQ ID NO 64
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 64
ggatagcagg aatatcgctt atttcctggc gatctcc                                37

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
ttcacataac tactgtcgcc gagcgcaatc                                         30

<210> SEQ ID NO 66
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
cgcaaaagaa aatgccgatt tgcggccgct attcctgcta tccttcgcgg                   50

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
caggaaataa gcgatattcc tgctatcctt cgcggca                                 37

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
tttggcgtcc acgatactga atttggagcg                                         30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
taacagtgaa ttcccgtaca tggtgccgac                                         30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
```
cacgtaaaga agcgcagaag tacatggacc                                        30

<210> SEQ ID NO 71
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
gtgctacgcc tgaataagtg cggccgcaca acgctcacgc cgaaaaatcc                   50

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
ctaacagaaa gcaacaacgc tcacgccgaa aaatcc                                  36

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
gtcagcatct ttgattttgc gctgagcagc                                         30

<210> SEQ ID NO 74
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
cgcaaaagaa aatgccgatt tgcggccgcc tttctgttag attccgccgc                   50

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
gcgtgagcgt tgttgctttc tgttagattc cgccgc                                  36

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
tatcaaacgg gcgatgattg ccgttgatgc                                         30

```
<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
tcttcatcct gctcgcggtt aaccagacgt                                          30

<210> SEQ ID NO 78
<211> LENGTH: 360
<212> TYPE: DNA
<213> ORGANISM: Escherichia coli

<400> SEQUENCE: 78
gagtcagaca acgaagtgaa catcaggatg atgacacttc tgcaggacac accaggatgg         60
tgtttcaggg aaaggcttct ggatgaagcg aagaggatga cgcaggacgc gttaaaggac        120
acctccagga tggagaatga gaaccggtca ggatgattcg gtgggtcagg aaggccaggg        180
acacttcagg atgaagtatc acatcggggt ggtgtgagca ggaagcaata gttcaggatg        240
aacgattggc cgcaaggcca gaggaaaagt tgtcaaggat gagcagggag caacaaaagt        300
agctggaatg ctgcgaaacg aaccgggagc gctgtgaata cagtgctccc ttttttttatt       360

<210> SEQ ID NO 79
<211> LENGTH: 245
<212> TYPE: DNA
<213> ORGANISM: Escherichia coli

<400> SEQUENCE: 79
atagagcgag gacgctaaca ggaacaatga ctcaggatga gggtcaggag cgccaggagg         60
cgaagacaga ggattgtcag gaagacaaac gtccggagac gtaattaaac ggaaatggaa        120
tcaacacgga ttgttccggc taaaggaaaa acagggtgtg ttggcggcct gcaaggattg        180
taagacccgt taagggttat gagtcaggaa aaaaggcgac agagtaatct gtcgcctttt        240
ttctt                                                                    245
```